(12) United States Patent
Lee et al.

(10) Patent No.: US 7,785,787 B2
(45) Date of Patent: Aug. 31, 2010

(54) METHODS OF ISOLATING AND AMPLIFYING NUCLEIC ACIDS USING SILANIZED SOLID SUPPORT

(75) Inventors: Myo-yong Lee, Suwon-si (KR); Joong-gun Lee, Seoul (KR); Young-nam Kwon, Gunpo-si (KR); Young-a Kim, Suwon-si (KR); Yeon-ja Cho, Seoul (KR); Shin-i Yoo, Gunpo-si (KR)

(73) Assignee: Samsung Electronics Co., Ltd. (KR)

( * ) Notice: Subject to any disclaimer, the term of this patent is extended or adjusted under 35 U.S.C. 154(b) by 23 days.

(21) Appl. No.: 11/345,174

(22) Filed: Feb. 1, 2006

(65) Prior Publication Data

US 2006/0264620 A1 Nov. 23, 2006

(30) Foreign Application Priority Data

Feb. 2, 2005 (KR) ............... 10-2005-0009741

(51) Int. Cl.
*C12Q 1/68* (2006.01)
*C12P 19/34* (2006.01)
(52) U.S. Cl. ........................... 435/6; 435/91.2
(58) Field of Classification Search ............... None
See application file for complete search history.

(56) References Cited

U.S. PATENT DOCUMENTS

| 5,234,809 | A | | 8/1993 | Boom et al. ............... 435/91 |
| 5,620,869 | A | * | 4/1997 | Woodard et al. ........... 435/91.1 |
| 5,622,896 | A | * | 4/1997 | Knotter et al. ............. 438/123 |
| 5,990,301 | A | | 11/1999 | Colpan et al. ............. 536/25.4 |
| 6,291,166 | B1 | | 9/2001 | Gerdes et al. ................ 435/6 |
| 2001/0014650 | A1 | * | 8/2001 | Smith et al. ................ 502/401 |
| 2003/0059819 | A1 | * | 3/2003 | Tzeng et al. ................ 435/6 |
| 2005/0142571 | A1 | * | 6/2005 | Parthasarathy et al. ....... 435/6 |

FOREIGN PATENT DOCUMENTS

| JP | 2000239599 A | * | 9/2000 |
| JP | 2002060671 A | * | 2/2002 |

OTHER PUBLICATIONS

Conzone and Pantano (Mar. 2004) Materials today pp. 20-26.*
Hencke et al. (1997) Nucleic Acid Res. vol. 25 No. 19 pp. 3957-3958.*
Weiler and Hoheisel (1996) Anal. Biochem. 243:218-227.*
Halliwell and Cass (2001) Anal. Chem. 73: 2476-2483.*
Liu et al. (2004) Anal. Chem. vol. 76: pp. 1824-1831.*
Liu et al. (2003) Proc. Micro-TAS 2003, Squaw Valley, CA, Oct. 5-9, 2003, 2003:pp. 1319-1322.*
Melzak, K.A.; Sherwood, C.S.; Turner, R.F.; Haynes, C.A. "Driving Forces for DNA Adsorption to Silica in Perchlorate Solutions" Journal of Colloid and Inerfacial Science 1996, vol. 181, pp. 635-644.
DeAngelis, M. M.; Wang, D.G.; Hawkins, T.L. "Solid-phase Reversible Immobilaization for the Isolation of PCR Products" Nucleic Acid Res. 1995, vol. 23, No. 22, pp. 4742-4743.
Adessi, C., Matton, G.; Ayala, G.; Turcatti, G.; Mermod, J.J.; Mayer, P.; Kawashima, E. "Solid Phase DNA Amplification: Characterization of Prior Attachment and Amplification" Nucleic Acid Res. 2000, vol. 28, No. 20, p. e87.
Huber, M.; Losert, D.; Hiller, R.; Harwanegg, C.; Mueller, M.W.; Schmidt, W.M. "Detection of Single Base Alterations in Genomic DNA by Solid Phase Polymerase Chain Reaction on Oligonucleotide Microarrays", Anal. Biochem. 2001, vol. 299, p. 24.
Mitterer, G.; Huber, M.; Leidinger, E.; Kirisits, C.; Lubitz, W.; Mueller, M.W.; Schmidt W.M. "Microarray-based Identification of Bacteria in Clinical Samples by Solid-phase PCR Amplification of 23S Ribosomal DNA Sequences," J. Clin. Microbiol. 2004, vol. 42, No. 3, p. 1048.
Boom, R.; Sol, C.J.A.; Salimans, M.M.M.; Jansen, C.L.; Wertheim-van Dillen, P.M.E.; van der Noordaa, J. "Rapid and Simple Method for Purification of Nucleic Acids", J. Clin. Microbiol. 1990, vol. 28, No. 3, pp. 495-503.

* cited by examiner

*Primary Examiner*—Kenneth R. Horlick
*Assistant Examiner*—David C Thomas
(74) *Attorney, Agent, or Firm*—Cantor Colburn LLP

(57) ABSTRACT

Provided are methods of isolating and amplifying nucleic acids from and in a nucleic acid-containing sample. The nucleic acid isolation method includes contacting a nucleic acid-containing sample to a silanized solid support to capture nucleic acids to the silanized solid support and treating the nucleic acid-captured solid support with an alkaline solution of pH 9 to 14. The nucleic acid amplification method includes contacting a nucleic acid-containing sample to a silanized solid support to capture nucleic acids to the silanized solid support; treating the nucleic acid-captured solid support with an alkaline solution of pH 9 to 14; and adding a nucleic acid amplification solution to the resultant solution after the alkaline solution treatment to perform nucleic acid amplification.

22 Claims, 5 Drawing Sheets

- : ANION EXCHANGER
- : DNA
- : SILANE COATING

BETAINE    SILANIZED SILICA BEAD

BEFORE ALKALINE TREATMENT

AFTER ALKALINE TREATMENT

PCR YIELD 1. 0.5M BETAINE
2. 0.1M BETAINE
3. 0.01M BETAINE
4. 0.001M BETAINE
5. CONTROL

1. CONTROL
2. λ DNA SEPARATED FROM BEAD + EcoRI
3. λ DNA SEPARATED FROM BEAD + EcoR I
4. UNDIGESTED λ DNA

15min @ 95°C in Tris buffer (pH 8)    15min @ 95°C in 0.1N NaOH 2    3                          1    2    3

1.  UNTREATED SILICA BEAD (CONTROL)
2.  SILANIZED BEAD + λ DNA
3.  SILANIZED BEAD + λ DNA

METHODS OF ISOLATING AND AMPLIFYING NUCLEIC ACIDS USING SILANIZED SOLID SUPPORT

CROSS-REFERENCE TO RELATED PATENT APPLICATION

This application claims priority from Korean Patent Application No. 10-2005-0009741, filed on Feb. 2, 2005, in the Korean Intellectual Property Office, the disclosure of which is incorporated herein in its entirety by reference.

1. Field Of The Invention

The present invention relates to methods of isolating and amplifying nucleic acids using a silanized solid support.

1. Description Of The Related Art

To perform amplification of desired targets after cell lysis, isolation of nucleic acids from a cell lysate containing proteins, etc. is required.

Some currently known representative DNA purification techniques are given below.

For example, isolation of nucleic acids from a nucleic acid-bound silica by washing and elution with a buffer is most widely used [Boom et al., U.S. Pat. No. 5,234,809, 1993, Boom et al., J. Clin. Micrbiol. 28(3), 495-503, 1990]. This method is based on the principle that nucleic acids of a nucleic acid-containing solution are bound to a surface of silica in the presence of a high concentration chaotropic salt such as GuHCl, NaI, or BuSCN, whereas they are separated from the nucleic acid-bound silica in the absence of a chaotropic salt or in the presence of a low concentration chaotropic salt. The precise elucidation of the interaction between two negatively charged materials, i.e., silica and nucleic acids, has not been carried out. However, the most persuasive elucidation is that binding between silica and nucleic acids is mediated by dehydration reaction [Melzak, K. A.; Sherwood, C. S.; Turner, R. F. B.; Haynes, C. A. Journal of Colloid and Interface Science 1996, 181, 635-644]. According to the elucidation of the binding between silica and nucleic acids based on dehydration reaction, both silica and nucleic acids are electrically negatively charged and thus are hydrophilic. Thus, silica and nucleic acids are surrounded by water molecules in a common solution. However, the presence of a high concentration chaotropic salt reduces the number of water molecules surrounding silica and nucleic acids due to stronger hydrophilicity of the chaotropic salt than the silica and the nucleic acids, resulting in binding of the silica and the nucleic acids. When a salt concentration is changed after the binding of silica and nucleic acids, i.e., when the nucleic acid-bound silica is contacted to a solution containing low concentration or no chaotropic salt, elution of the nucleic acids from the silica occurs. Such reversible nucleic acid binding and elution can be efficiently used in purification and isolation of nucleic acids. However, a chaotropic salt is very toxic and acts as an inhibitor against a subsequent process such as PCR, and thus, is required to be removed after used.

There is also known a technique of isolating and purifying nucleic acids by reversible binding of polyethyleneglycol (PEG) with the nucleic acids [Hawkins et al., Nucleic Acids Res. 1995(23):4742-4743]. This technique is based on solid phase reversible immobilization (SPRI). That is, a carboxyl group-coated solid, for example, a carboxyl group-coated magnetic bead is contacted to a high concentration PEG to form a PEG-immobilized magnetic bead, resulting in binding of nucleic acids with the PEG-immobilized magnetic bead. The nucleic acid-bound bead is separated and then subjected to nucleic acid elution in a low-concentration salt condition. This technique is also based on salt concentration adjustment. That is, nucleic acid binding occurs in a high concentration salt condition, whereas nucleic acid elution occurs in a low concentration salt condition.

There is also known a technique of binding nucleic acids to a solid support using a positively charged material, i.e., alumina, i.e., a technique of capturing nucleic acids using alumina coated on an inner wall of a microtube [U.S. Pat. No. 6,291,166, Xtrana]. According to this technique, the binding of nucleic acids to alumina is very strong and irreversible. Therefore, separation of nucleic acids from alumina is difficult, and thus, amplification of nucleic acids occurs on the alumina. Even though extraction, purification, and amplification of nucleic acids are easily performed in one pot, there arises a problem that solid-phase PCR yield may be remarkably reduced.

In addition, U.S. Pat. No. 5,990,301 (Qiagen) discloses a method of isolating DNAs by anion exchange reaction. However, this method involves a complicated elution procedure for obtaining desired DNAs. That is, since it is difficult to separate DNAs captured on an anion exchanger, precise adjustment of salt concentration during elution and separate precipitation with alcohol for salt filtration are required.

As described above, common DNA isolation techniques capture nucleic acids based on charge property of the nucleic acids or using an additional chemical substance (chaotropic salt, PEG, etc.), which renders DNA elution difficult. Furthermore, since DNA isolation and purification are accomplished by several processes using buffers with different compositions, applications to LOC (Lab-On-a-Chip) or LIP (Lab-In-Package) may be difficult.

SUMMARY OF THE INVENTION

The present invention provides a method of isolating nucleic acids at high efficiency and with easiness that can increase a product yield of subsequent PCR. The present invention also provides a method of amplifying nucleic acids that can increase PCR yield.

According to an aspect of the present invention, there is provided a method of isolating nucleic acids from a nucleic acid-containing sample, the method including: contacting a nucleic acid-containing sample to a silanized solid support to capture nucleic acids to the silanized solid support; and treating the nucleic acid-captured solid support with an alkaline solution of pH 9 to 14.

The method may further include heating the nucleic acid-captured solid support at 40 to 100° C. after treatment with the alkaline solution.

According to another aspect of the present invention, there is provided a method of amplifying nucleic acids in a nucleic acid-containing sample, the method including: contacting a nucleic acid-containing sample to a silanized solid support to capture nucleic acids to the silanized solid support; treating the nucleic acid-captured solid support with an alkaline solution of pH 9 to 14; and adding a nucleic acid amplification solution to the resultant solution after the alkaline solution treatment to perform nucleic acid amplification.

The method may further include heating the nucleic acid-captured solid support at 40 to 100° C. after treatment with the alkaline solution.

The nucleic acid amplification may be performed without removing the solid support.

The content of silane may be in the range from 0.0001 to 1% by volume based on the total volume of the resultant solution after the alkaline solution treatment.

The nucleic acid-containing sample may include at least one selected from the group consisting of double-stranded DNAs, single-stranded DNAs, plasmid DNAs, and RNAs.

The solid support is not particularly limited provided that has a silinizable solid surface and may be made of silica, glass, plastic, silicone, iron oxide, aluminum oxide, titanium oxide, or zirconium oxide. The form of the solid support is not particularly limited and may be bead, pillar, or plate.

The operation of contacting the nucleic acid-containing sample to the silanized solid support to capture the nucleic acids to the silanized solid support may be performed using an anionic exchanger.

The silanized solid support may include an anion exchanger on a surface thereof. The anion exchanger may have a monoalkylamino group, a dialkylamino group, or a quaternary alkylamino group. The anion exchanger may be betaine attached to a surface of the silanized solid support via an amide bond.

The solid support may have a magnetic property.

The alkaline solution may be a NaOH solution, a Tris buffer solution, a borate buffer solution, or a carbonate buffer solution.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in more detail.

According to the present invention, isolation and purification of nucleic acids can be performed even without using a toxic substance such as a chaotropic salt and EtBr unlike a conventional technique. Furthermore, unlike a conventional technique which cannot easily elute nucleic acids due to nucleic acid capturing by charge-charge interaction, nucleic acid isolation can be efficiently performed even without an elution process, and thus isolated nucleic acids can be directly used in-a subsequent PCR process. In addition, according to a nucleic acid isolation method of the present invention, a PCR inhibitor lowering PCR yield is not used. To provide the above advantages, in the present invention, nucleic acids are captured on a silanized solid support and treated with alkaline to isolate a nucleic acid-bound silane layer from the solid support. The nucleic acid-bound silane layer is directly used in amplification reaction without further separation or purification. According to the present invention, the isolation and PCR of nucleic acids can also be performed on the same substrate.

In a conventional technique, nucleic acid capturing and separation are performed by adjusting a salt concentration. However, according to the present invention, PCR can be efficiently performed even without a salt concentration adjustment for nucleic acid isolation.

Therefore, the present invention provides a method of isolating nucleic acids from a nucleic acid-containing sample, the method including:

contacting a nucleic acid-containing sample to a silanized solid support to capture nucleic acids to the silanized solid support; and treating the nucleic acid-captured solid support with an alkaline solution of pH 9-14.

Figure 1:
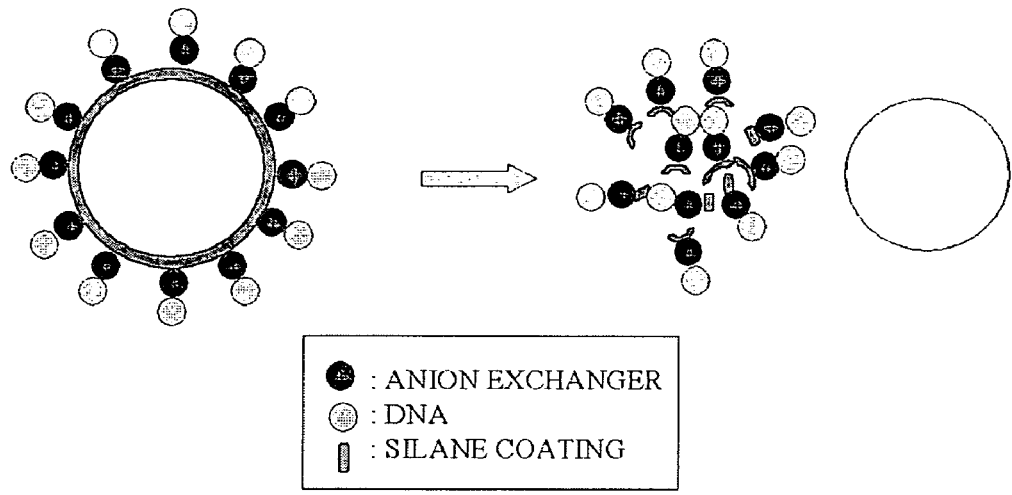
FIG. 1 is a schematic diagram illustrating nucleic acid isolation according to an embodiment of the present invention.

An example of a nucleic acid isolation method of the present invention is illustrated in FIG. 1. Referring to FIG. 1, a surface of a solid support, e.g., a bead is silanized. Then, a nucleic acid-capturing compound, e.g., an anion exchanger is bound to the silanized bead. In this state, when a DNA-containing sample is added, DNAs are bound to the anion exchanger. When a thus produced DNA-bound bead is treated with alkaline and/or heat, a surface silane layer of the bead is detached from the bead, together with the anion exchanger and DNAs, thereby resulting in production of silane-anion exchanger-DNA complex fragments as shown in FIG. 1. These fragments can be directly used for PCR after being recovered.

In a conventional nucleic acid purification method using an anion exchanger, elution of nucleic acids captured on an anion exchanger is not an easy task and requires the use of a separate buffer and a high concentration salt solution. However, according to the nucleic acid isolation method of the present invention, DNA elution is not required, DNAs can be easily separated by silane coating delamination, and a PCR inhibitor, e.g., a buffer, which may adversely affect a subsequent PCR, is not used.

The nucleic acid-containing sample that can be used herein may include double-stranded DNAs, single-stranded DNAs, plasmid DNAs, or RNAs.

Preferably, the nucleic acid isolation method of the present invention may further include heating the nucleic acid-captured solid support during or after treatment with the alkaline solution. Heating at 40 to 100° C. can facilitate delamination of the silane coating.

In the nucleic acid isolation method of the present invention, there are no limitations on the solid support provided that can be surface-silanized. For example, the solid support may be made of metal oxide such as silicone, glass, silica, diamond, quartz, alumina, platinum oxide, aluminum oxide, zirconium oxide, and tungsten oxide. The form and size of the solid support are not particularly limited. For example, the solid support may be in the form of flat board, wafer, fiber, bead, particle, chain, gel, sheet, sphere, pad, pillar, slide, thin film, or plate. The solid support may also be in the form of a capillary tube, a channel, a membrane, a test tube, a column, a pin, or a glass fiber. A silica bead is preferable.

Figure 2:
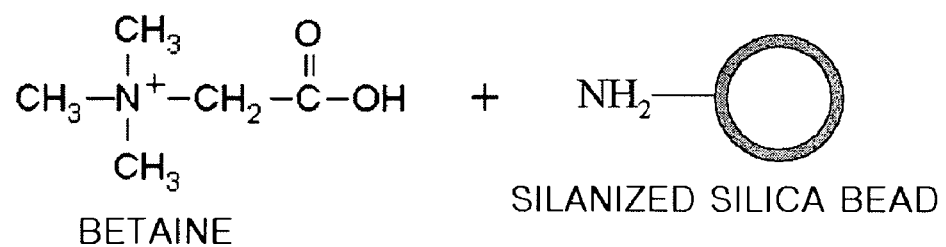
FIG. 2 is a view illustrating a reaction scheme of an amino-silanized silica bead and betaine used as an anion exchanger according to an embodiment of the present invention.
Figure 2:
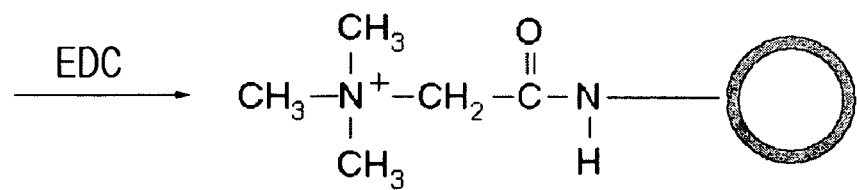

In the nucleic acid isolation method of the present invention, the solid support is silanized. Silanization may be performed by a known method. For example, reference may be made to the following documents: C line Adessi et al. (2000) Solid phase DNA amplification: characterisation of primer attachment and amplification, Nucleic Acids Res., 28, e87.; Martin Huber et al. (2001) Detection of single base alterations in genomic DNA by solid phase polymerase chain reaction on oligonucleotide microarrays, Anal. Biochem., 299, 24.; Georg Mitterer et al. (2004) Microarray-based identification of bacteria in clinical samples by solid-phase PCR amplification of 23S ribosomal DNA sequences, J. Clin. Microbiol. 42, 1048. If necessary, the silane coating may have a functional group, such as an amino group, as shown in FIG. 2. The silanized solid support can directly capture nucleic acids or bind with a nucleic acid-capturing compound via the functional group.

A compound capable of binding with a silane layer and capturing nucleic acids is not particularly limited provided that is a nucleic acid-binding functional group or compound. An anion exchanger is preferable. A preferable anion exchanger that can be used herein is a material having a monoalkylamino group, a dialkylamino group, or a quaternary alkylamino group. Betaine is more preferable since it prevents secondary structure formation during subsequent PCR, thereby stabilizing DNA amplification.

FIG. 2 illustrates a reaction scheme of an amino-silanized silica bead and betaine according to an embodiment of the present invention. Referring to FIG. 2, an amino group of the amino-silanized silica bead reacts with a carboxyl group of betaine in the presence of a cross-linker, 1-ethyl-3-(3-dimethylaminopropyl)carbodiimide (EDC), to link betaine to the silica bead via an amide bond. The action mechanism of EDC used as the cross-linker is represented by the following reaction scheme 1:

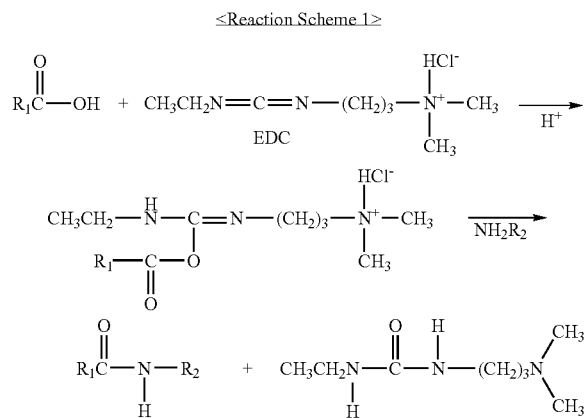

A nucleic acid-containing sample is added to an anion exchanger-bound silica bead and treated with alkaline and/or heat to separate a silane coating layer from the silica bead. The alkaline treatment may be performed at pH of 9 to 14. As described above, in the nucleic acid isolation method of the present invention, the silane coating layer can be easily separated from the silica bead by alkaline treatment without a separate elution process, leading to easy nucleic acid isolation.

The silane coating layer separated from the silica bead contains both an anion exchanger and nucleic acids. If a magnetic bead is used, only the magnetic bead can be separated using magnetic property of the bead. An anion exchanger-nucleic acid complex thus obtained can be directly subjected to PCR by a common method. As described above, according to the present invention, PCR can also be performed in a bead-containing solution.

The above-described embodiments of the present invention can be modified without departing from the spirit and scope of the present invention as defined by the following claims.

Hereinafter, the present invention will be described more specifically with reference to the following examples.

EXAMPLES

Example 1

-Preparation of Anion Exchanger-bound Silica Beads

Silica beads (3 μm in diameter, Bangs Laboratories, Inc., Fishers, Ind., US) were silanized with aminopropyltriethoxysilane as follows.

That is, the silica beads were three times washed with acetone, treated with a solution of 10% aminoproyltriethoxysilane in acetone at room temperature for two hours, and washed with acetone and PBS buffer.

Then, the silanized silica beads were allowed to react with betaine in the presence of 0.4M EDC used as a linker at room temperature in a 0.05 M MES buffer for 3 hours, to obtain betaine-bound silica beads (see FIG. 2).

-Binding of Silica Beads with DNAs

2 μl (539 ng/L) of 50 kb λ DNAs (Promega) were loaded in a microtube and 58 μl of a PBS solution was added thereto. The resultant DNA solution was mixed with 2.9 mg of the silanized silica beads and stirred at room temperature for 15 minutes.

Figure 3:
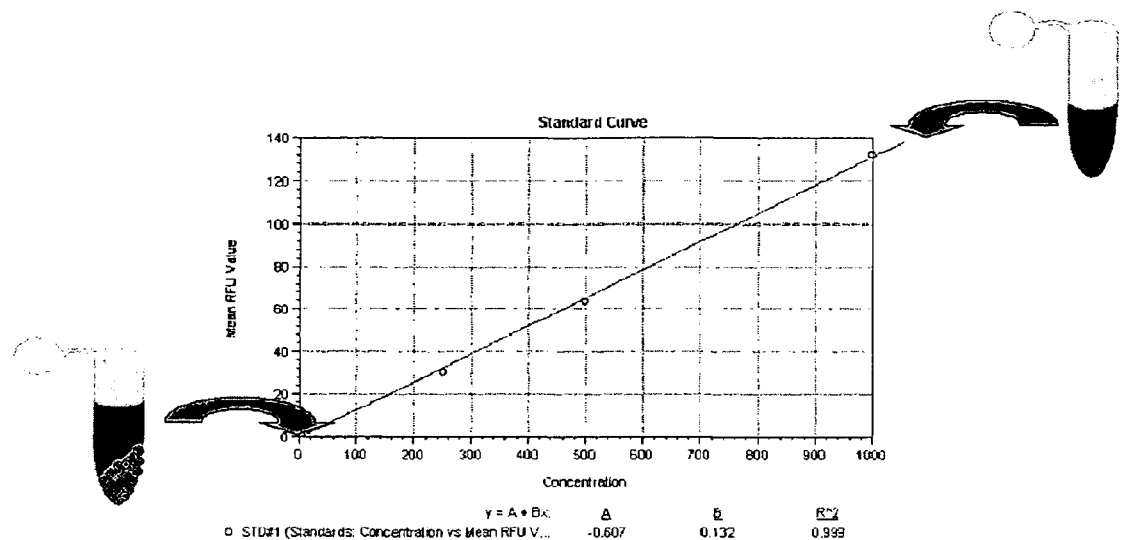
FIG. 3 is a graph illustrating a fluorescent intensity of residual DNAs after binding of DNAs with a silanized bead prepared according to an embodiment of the present invention.

Then, to evaluate degree of DNA binding, before and after mixing of the DNA solution with the silanized silica beads, a DNA quantitative reagent, PicoGreen (Molecular Probes, Inc.) was added and fluorescence was measured using Microplate Fluorometer (Molecular Devices). The results are shown in FIG. 3. Referring to FIG. 3, after mixing of the DNA solution with the silanized silica beads, DNA quantitative analysis showed that an aqueous part of the mixture solution contained no DNAs.

-Removal of Silane Coating Layers from Silica Beads

The DNA-bound silica beads were centrifuged and treated with 60 μl of Tris buffer (pH 8, Bioneer, Daejon, Korea) for 15 minutes at 95° C.

Figure 9:
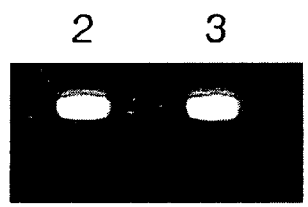
FIG. 9 is agarose gel electrophoretic patterns of DNA-bound beads obtained according to a method of the present invention after treatment with two alkaline solutions with different pH.
Figure 9:
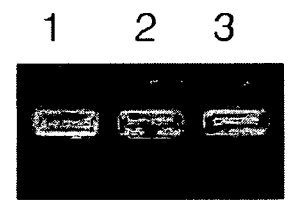

In another experiment, the DNA-bound silica beads were centrifuged and treated with 60 μl of a 0.1 N NaOH solution at 95° C. for 15 minutes. The resultant beads of the two experiments were loaded into agarose gel wells, stained with EtBr, and visualized by UV exposure. The results are shown in FIG. 9. Referring to FIG. 9, no removal of silane coating from the beads was observed in the DNA-bound silica beads treated with the Tris buffer (pH 8).

Figure 4:
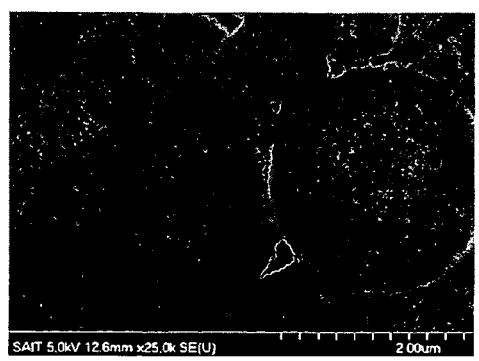
FIG. 4 is a Scanning Electron Microscopic (SEM) image of silanized beads before and after alkaline treatment.
Figure 4:
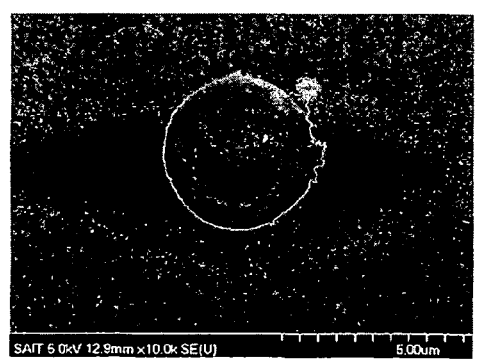

In this regard, to more specifically explain the present invention, Scanning Electron Microscopic (SEM) images of silanized beads before and after alkaline treatment are shown in FIG. 4. Referring to FIG. 4, removal of silane coating from the beads was observed with a naked eye.

Example 2

According to the same manner as in Example 1, 2.9 mg of silanized beads were allowed to react with 400 ng of HBV plasmid DNAs, washed with PBS buffer, and centrifuged to thereby collect the resultant beads. The collected beads were added to 39 μl of a 0.1 N NaOH solution and heated to remove silane coating from the beads. The resultant solution was again centrifuged to take a supernatant. The supernatant was neutralized by addition of 1 μl of 1 M Tri-HCl (pH7). PCR for 1 μl of the resultant neutralization solution was performed as follows.

The following PCR primers were used:

```
primer A
(5-AGTGTGGATTCGCACTCCT-3);        (SEQ ID NO: 1)
and primer B
(5-GAGTTCTTCTTCTAGGGGACCTG-3).    (SEQ ID NO: 2)
```

PCR was performed using Taq polymerase (Takara, Solgent, Korea) as follows: pre-denaturation at 95° C. for 5 minutes, 25 cycles (denaturation at 95° C. for 30 seconds, annealing at 62° C. for 15 seconds, and extension at 72° C. for 30 seconds), and additional extension at 72° C. for 3 minutes.

Figure 5:
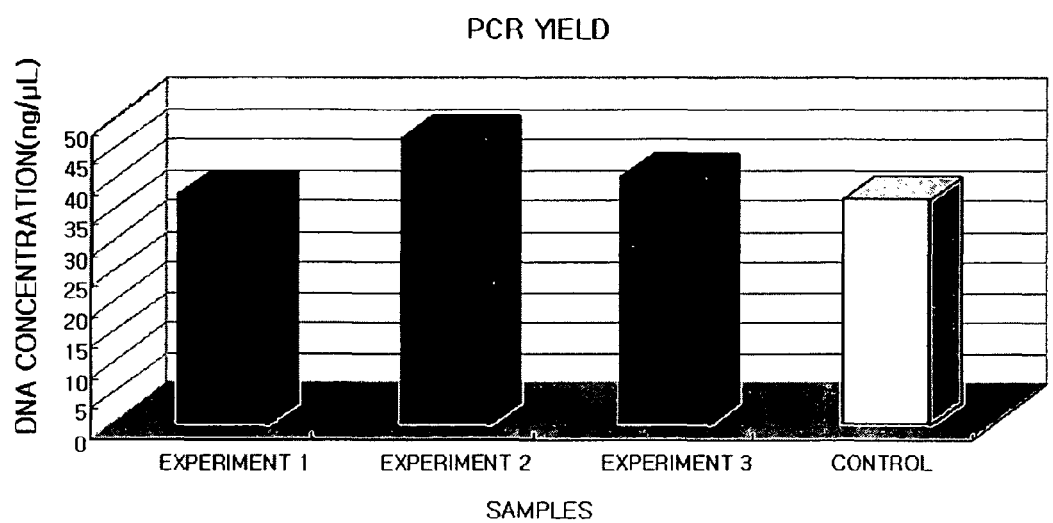
FIG. 5 is a comparative graph illustrating PCR result for DNAs isolated according to a method of the present invention and PCR result for control.
Figure 6:
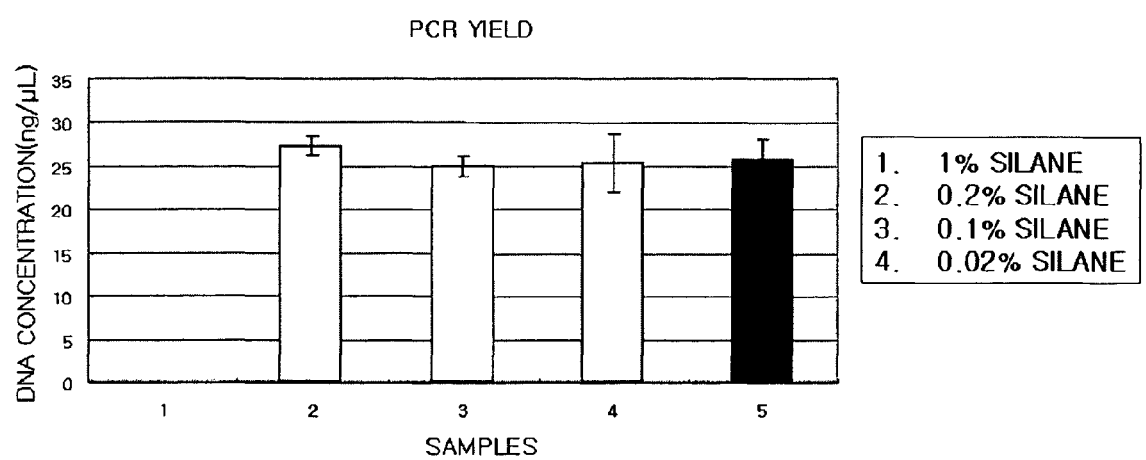
FIG. 6 is a graph illustrating a PCR yield with respect to silane concentration.

The above experiment was repeated three times (designated "experiments 1, 2, and 3"), and then DNA concentration for each experiment was measured to evaluate PCR yield. The results are shown in FIG. 5. In FIG. 5, PCR result for the same amount of untreated DNAs was used as control. Referring to FIG. 5, there was little difference in PCR yield between the control and the experiments 1, 2, and 3. FIG. 6 is a graph illustrating a PCR yield with respect to the concentration of silane remained in a solution after alkaline treatment. Referring to FIG. 6, it can be seen that silane concentration of less than 1% (percentage of silane volume to solution volume after alkaline treatment) does not adversely affect PCR.

Thus, it can be seen that DNA isolation and PCR can be performed in one pot.

Example 3

EcoRI Treatment

Figure 8:
FIG. 8 is agarose gel electrophoretic patterns of EcoRI digests of λ DNA.

In this Example, 1 g of λ DNA obtained in Example 1 was used as a DNA sample. The DNA sample was digested with 5 units of EcoRI (NEN Life Science Products, Boston, Mass.) at 37° C. for one hour and then run on 1% agarose gel. As a result, electrophoretic patterns of FIG. 8 were obtained (see lanes 2 and 3). In FIG. 8, lane 1 represents 5 units of EcoRI digests of 1 g of untreated λ DNA and lane 4 represents undigested λ DNA. Referring to FIG. 8, when λ DNA obtained according to a nucleic acid isolation method of the present invention was treated with restriction enzyme (lanes 2 and 3), the same electrophoretic patterns as lane 1 were obtained, which demonstrates non-toxic effect of the nucleic acid isolation method of the present invention.

According to the present invention, isolation and purification of nucleic acids can be performed even without using a toxic substance such as a chaotropic salt and EtBr unlike a conventional technique. Furthermore, unlike a conventional technique which cannot easily elute nucleic acids due to nucleic acid capturing by charge-charge interaction, nucleic acid isolation can be efficiently performed even without an elution process, and thus, isolated nucleic acids can be directly used in a subsequent PCR process. In addition, according to a nucleic acid isolation method of the present invention, a PCR inhibitor lowering PCR yield is not used.

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
agtgtggatt cgcactcct                                              19

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
gagttcttct tctaggggac ctg                                         23
```

Figure 7:
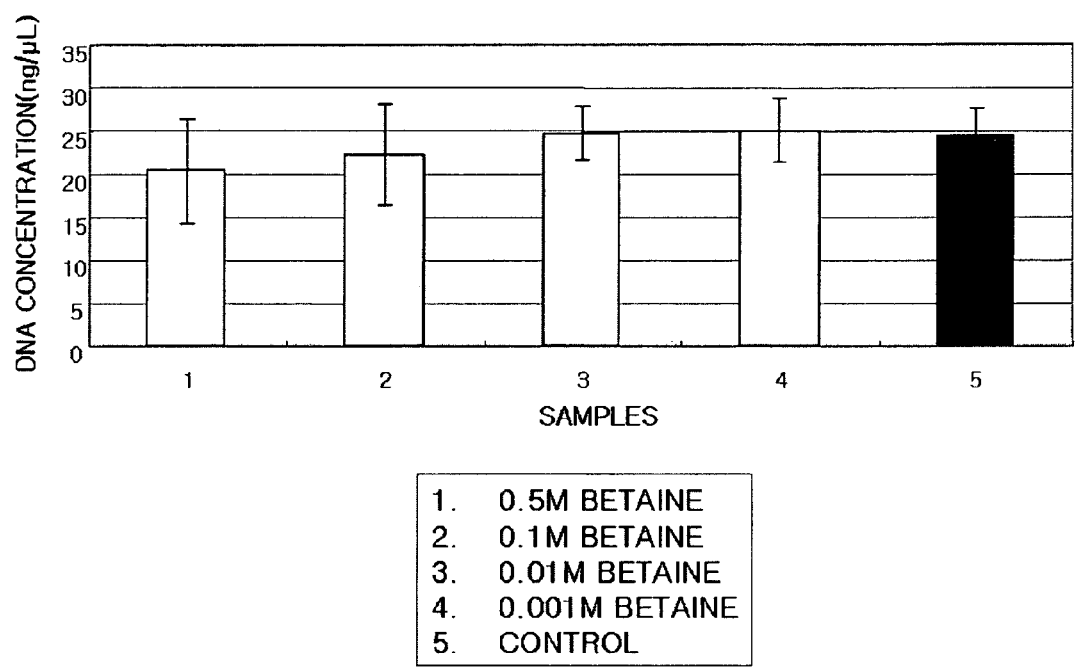
FIG. 7 is a graph illustrating a PCR yield with respect to betaine concentration.

FIG. 7 is a graph illustrating a PCR yield with respect to the concentration of betaine remained in a solution after alkaline treatment. Referring to FIG. 7, it can be seen that PCR yield is not significantly affected by betaine concentration.

The experimental results of FIGS. 6 and 7 show that materials used for DNA isolation do not affect subsequent PCR.

What is claimed is:

1. A method of isolating nucleic acids from a nucleic acid-containing sample, the method comprising:

reacting an anion exchanger with a silanized solid support to form a silane-anion exchanger complex;

contacting a nucleic acid-containing sample to the silane-anion exchanger complex formed on the silanized solid support to capture nucleic acids to form a silane-anion exchanger-nucleic acid complex; and treating the silanized solid support with an alkaline solution of pH 9 to 14 such that the silane layer is removed from the solid support resulting in removal of the silane-anion exchanger-nucleic acid complex, wherein the content of silane is in the range from 0.0001 to less than 1% by volume based on the total of the resultant solution after the alkaline solution treatment.

2. The method of claim 1, further comprising heating the solid support at 40 to 100° C. after treatment with the alkaline solution.

3. The method of claim 1, wherein the nucleic acid-containing sample comprises at least one selected from the group consisting of double-stranded DNAs, single-stranded DNAs, plasmid DNAs, and RNAs.

4. The method of claim 1, wherein the solid support is made of silica, glass, plastic, silicone, iron oxide, aluminum oxide, titanium oxide, or zirconium oxide.

5. The method of claim 1, wherein the solid support is in the form of bead, pillar, or plate.

6. The method of claim 1, wherein the anion exchanger has a monoalkylamino group, a dialkylamino group, or a quaternary alkylamino group.

7. The method of claim 1, wherein the anion exchanger is betaine attached to a surface of the silanized solid support via an amide bond.

8. A method of amplifying nucleic acids in a nucleic acid-containing sample, the method comprising:

reacting an anion exchanger with a silanized solid support to form a silane-anion exchanger complex;

contacting a nucleic acid-containing sample to the silane-anion exchanger complex formed on the silanized solid support to capture nucleic acids to form a silane-anion exchanger-nucleic acid complex;

treating the silanized solid support with an alkaline solution of pH 9 to 14 such that the silane layer is removed from the solid support resulting in removal of the silane-anion exchanger-nucleic acid complex, wherein the silane-anion exchanger-nucleic acid complex is used without elution for subsequent amplification so that the isolation of nucleic acid and amplification thereof are performed in a single vessel;

adding a nucleic acid amplification solution to the resultant solution after the alkaline solution treatment to perform nucleic acid amplification; and amplifying the nucleic acids.

9. The method of claim 8, further comprising heating the solid support at 40 to 100° C. after treatment with the alkaline solution.

10. The method of claim 8, wherein the content of silane is in the range from 0.0001 to less than 1% by volume based on the total volume of the resultant solution after the alkaline solution treatment.

11. The method of claim 8, wherein the anion exchanger has a monoalkylamino group, a dialkylamino group, or a quaternary alkylamino group.

12. The method of claim 8, wherein the anion exchanger is betaine attached to a surface of the silanized solid support via an amide bond.

13. The method of claim 2, wherein the nucleic acid-containing sample comprises at least one selected from the group consisting of double-stranded DNAs, single-stranded DNAs, plasmid DNAs, and RNAs.

14. The method of claim 2, wherein the solid support is made of silica, glass, plastic, silicone, iron oxide, aluminum oxide, titanium oxide, or zirconium oxide.

15. The method of claim 2, wherein the solid support is in the form of bead, pillar, or plate.

16. The method of claim 2, wherein the anion exchanger has a monoalkylamino group, a dialkylamino group, or a quaternary alkylamino group.

17. The method of claim 2, wherein the anion exchanger is betaine attached to a surface of the silanized solid support via an amide bond.

18. The method of claim 9, wherein the content of silane is in the range from 0.0001 to less than 1% by volume based on the total volume of the resultant solution after the alkaline solution treatment.

19. The method of claim 9, wherein the anion exchanger has a monoalkylamino group, a dialkylamino group, or a quaternary alkylamino group.

20. The method of claim 9, wherein the anion exchanger is betaine attached to a surface of the silanized solid support via an amide bond.

21. The method of claim 1, wherein the method is implement on a lab-on-a-chip or a lab-in-package.

22. The method of claim 8, wherein the method is implement on a lab-on-a-chip or a lab-in-package.

* * * * *